（12） United States Patent
Brahm et al.

(10) Patent No.: US 10,687,865 B2
(45) Date of Patent: Jun. 23, 2020

(54) SPINAL GRAFT

(71) Applicant: Brahm Holdings, LLC, Germantown, TN (US)

(72) Inventors: Timothy R. Brahm, Germantown, TN (US); Patrick Curlee, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 0 days.

(21) Appl. No.: 15/852,349

(22) Filed: Dec. 22, 2017

(65) Prior Publication Data

US 2018/0132908 A1     May 17, 2018

Related U.S. Application Data

(63) Continuation of application No. 14/710,650, filed on May 13, 2015, now Pat. No. 9,867,641.

(60) Provisional application No. 61/993,485, filed on May 15, 2014.

(51) Int. Cl.
*A61B 17/70*      (2006.01)
*G09B 19/00*      (2006.01)
*A61B 17/00*      (2006.01)

(52) U.S. Cl.
CPC ...... *A61B 17/7062* (2013.01); *A61B 17/7067* (2013.01); *G09B 19/00* (2013.01); *A61B 2017/00004* (2013.01)

(58) Field of Classification Search
CPC ............. A61B 17/7062; A61B 17/7067; A61F 2210/0004; A61F 2002/2835
See application file for complete search history.

(56) References Cited

U.S. PATENT DOCUMENTS

| | | | |
|---|---|---|---|
| 7,862,590 B2 * | 1/2011 | Lim | A61B 17/7067 606/248 |
| 8,029,550 B2 * | 10/2011 | Dewey | A61B 17/7067 606/248 |
| 2002/0173850 A1 * | 11/2002 | Brodke | A61F 2/30767 623/17.11 |
| 2007/0093823 A1 * | 4/2007 | Booth | A61B 17/7062 606/249 |
| 2008/0019970 A1 | 1/2008 | Gorman | |
| 2010/0119492 A1 * | 5/2010 | Hans | A61L 27/12 424/93.7 |
| 2011/0160772 A1 | 6/2011 | Arcenio | |
| 2012/0109201 A1 * | 5/2012 | Kretzer | A61B 17/7049 606/248 |
| 2013/0184826 A1 | 7/2013 | Thaiyananthan | |

\* cited by examiner

*Primary Examiner* — Julianna N Harvey
(74) *Attorney, Agent, or Firm* — Barnes & Thornburg LLC

(57) ABSTRACT

Provided herein is a spinal graft that fuses to and stabilizes the spine upon placement thereby helping to prevent spinal stenosis recurrence and eliminating pain associated with an unstable spine. The graft may be coated with a human birth tissue composition. Also provided herein are methods of stabilizing the spine after decompression surgery.

9 Claims, 3 Drawing Sheets

SPINAL GRAFT

CROSS-REFERENCE TO RELATED APPLICATIONS

This application is a Continuation of U.S. application Ser. No. 14/710,650 filed May 13, 2015, which claims the benefit of U.S. Provisional Application No. 61/993,485 filed May 15, 2014, the contents of each are incorporated herein by reference in its entirety.

FIELD OF THE INVENTION

A graft that maintains spacing between a superior vertebra and inferior vertebra following surgical intervention involving the laminae is provided. Methods for stabilizing the spine following such surgery are also provided.

BACKGROUND OF THE INVENTION

Spinal stenosis, a narrowing of the spinal canal, may result in pain, numbness, and muscle weakness in the limbs. The condition affects elderly people primarily and is caused by degenerative changes in the body that cause enlargement of the facet joints and thickening of the ligaments resulting in constriction of the spinal cord and nerves. Such constriction may be relieved by surgical intervention such as a spinal decompression procedure.

Spinal decompression surgery may be performed anywhere along the spine to remove any structures that are compressing the nerves in the spinal canal or vertebral foramen (opening through which the spinal cord passes). Lamina, the bone that forms the backside of the spinal canal, may be removed along with other soft tissues to allow for more room for the nerves. The laminae are a part of the posterior arch of the vertebrae. The laminae comprise two flattened plates that extend medially from the pedicles and meet at the spinous process to form the posterior wall of the spinal foramen. Depending on the extent of stenosis, one of a variety of decompression surgeries may be performed including laminectomy, laminotomy, foraminotomy, or laminaplasty. Spinal fusion, a surgical technique used to join two or more vertebrae, is another surgical intervention option that is often performed in combination with such decompression procedures to immobilize the affected vertebrae and stabilize sections of the spine. Fusion may use a combination of bone graft(s), rods and screws to connect to vertebrae together, thereby inducing bony incorporation and healing the vertebrae together as one piece of bone. Fusion helps prevent recurrence of spinal stenosis and aids in eliminating pain arising from an unstable spine. Supplementary bone tissue (e.g., autologous iliac crest bone, allograft tissue, synthetic cage with bone substitute filler) is used in conjunction with the body's natural bone growth processes to fuse the vertebrae. However, autologous tissue recovery often leads to graft site morbidity. Furthermore, fusion often leads to adjacent segment disease, which may limit the duration of success of the operation. Thus, there remains a need for safe, effective grafts as well as methods for treating the spine after surgical intervention for conditions such as spinal stenosis.

SUMMARY OF THE INVENTION

Provided herein is a spinal graft that fuses to and stabilizes the spine upon placement thereby helping to prevent spinal stenosis recurrence and eliminating pain associated with an unstable spine. According to one aspect, the graft includes a superior arm having a surface defining a notch positioned at a central region of the superior arm to receive and contact against an inferior edge of a spinous process of a superior vertebra, an inferior arm having a surface defining a notch positioned at a central region of the inferior arm to receive and contact against a superior edge of a spinous process of an inferior vertebra, a first wing for extending into a first vertebral gutter; and a second wing for extending into a second vertebral gutter. According to one embodiment, the graft may include at least one area defining an opening for receiving at least one screw for securing the graft. According to one embodiment, the at least one opening may be located in each of the first and second wings such that a screw is secured within the first and second vertebral gutters. According to one embodiment, the graft is prepared from cancellous bone, demineralized cancellous bone, allograft (fresh or fresh-frozen), freeze dried bone allograft, demineralized freeze dried bone allograft, cortical cancellous bone, or a combination thereof. According to one embodiment, the graft further includes an effective amount of a human birth tissue material composition deposited on an outer surface of the graft. According to one embodiment, the birth tissue material composition comprises one or more components of the placental organ. According to one embodiment, the one or more of the components of the placental organ is the placental globe, the umbilical cord, the umbilical cord blood, the chorionic membrane, the amniotic membrane, the Wharton's jelly, the amniotic fluid, and other placental gelatins, cells, or extracellular material.

According to another aspect, a method of stabilizing a vertebral region of a spine following a decompression surgery is provided. According to one embodiment, the method includes the steps of performing a decompression surgery, providing the graft as provided herein, engaging the notch of the superior arm with an inferior edge of a spinous process of a superior vertebra, and engaging the notch of the inferior arm with an superior edge of a spinous process of an inferior vertebra. According to such an embodiment, the vertebral region of the spine is stabilized. According to one embodiment, the method further includes the step of securing the graft to the vertebral region with at least one screw, rod, plate, or a combination thereof.

According to another aspect, a kit for stabilizing the spine following a decompression surgery is provided. According to one embodiment, the kit includes a graft as provided herein, optionally, at least one screw, rod, or combination thereof for securing the graft to the spine, and instructions for use thereof.

DETAILED DESCRIPTION OF THE INVENTION

Figure 1:
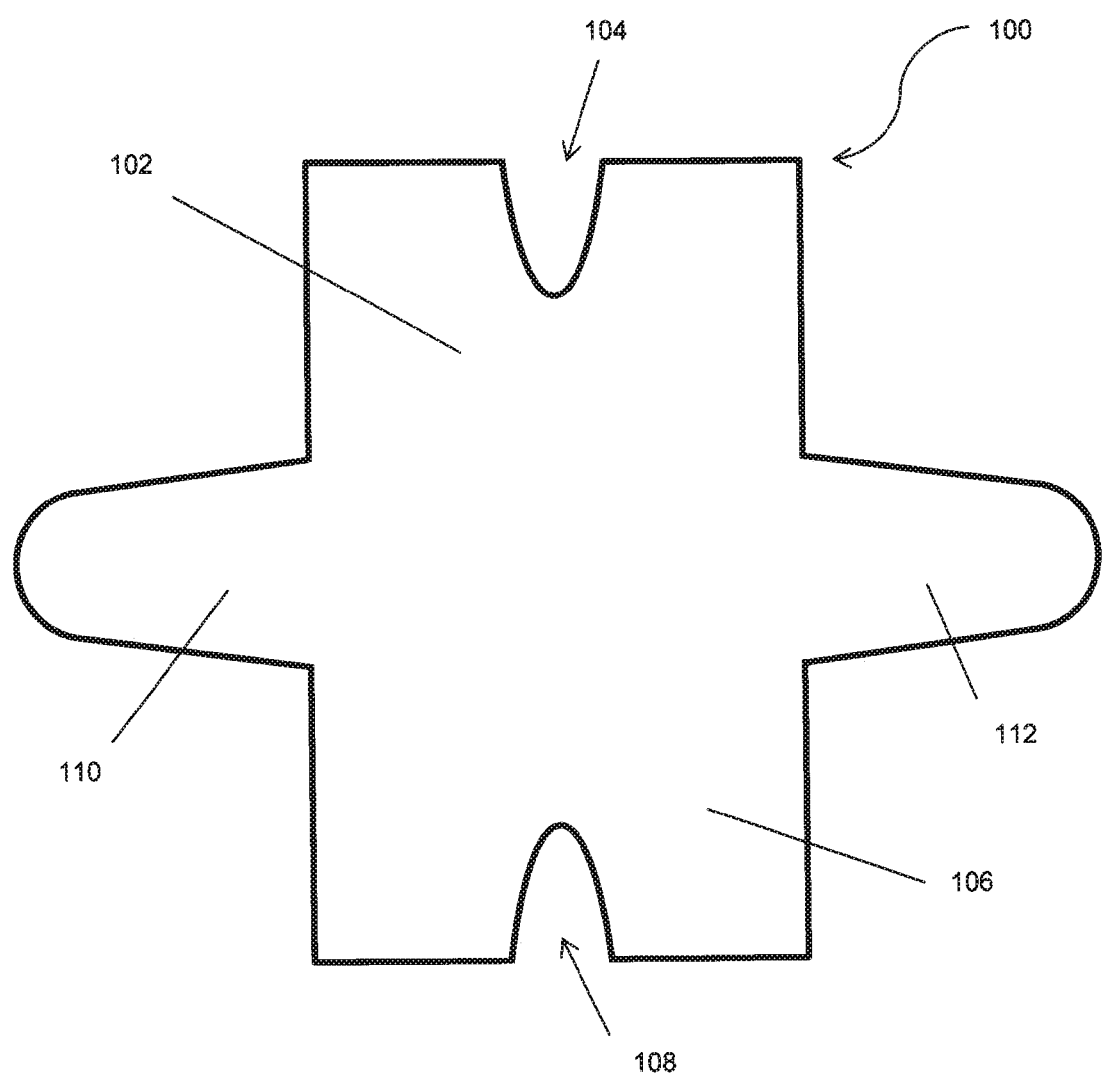
FIG. 1 is a front view of a graft according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, "human birth tissue" encompasses one or more of the components of the placental organ including, but not limited to, the placental globe, the umbilical cord, the umbilical cord blood, the chorionic membrane, the amniotic membrane, the Wharton's jelly, the amniotic fluid, and other placental gelatins, cells, and extracellular material.

As used herein, "placental tissue components" encompass one or more of the tissue components of the placental organ including, but not limited to, the placental globe, the umbilical cord, the umbilical cord blood, the chorionic membrane, the amniotic membrane, the Wharton's jelly and other placental gelatins, cells and extracellular material.

As used herein, the term "amnion" and "amniotic membrane" are used interchangeably.

As used herein, the term "effective amount" refers to an amount of a particular composition sufficient to elicit the desired therapeutic effects.

As used herein, the term "decompression surgery" refers to laminectomy, laminotomy, foraminotomy, laminaplasty, or other spinal surgery where spinal fusion or stabilization interventions may be utilized.

As used herein, the term "laminectomy" refers to the surgical procedure for removing the entire lamina, a portion of the facet joints, and any thickened ligaments overlying the spinal cord and nerves.

As used herein, the term "laminotomy" refers to the surgical procedure for removing a small portion of the lamina and ligaments, usually on a single side.

As used herein, the term "foraminotomy" refers to the surgical procedure for removal of bone around the neural foramen and can be performed with a laminectomy or laminotomy.

As used herein, the term "laminaplasty" refers to the surgical procedure for the expansion of the spinal canal by cutting the laminae on one side and swinging the laminae open.

Provided herein is a spinal graft that fuses to and stabilizes the spine upon placement, thereby helping to prevent spinal stenosis recurrence and eliminating pain associated with an unstable spine. The graft as provided herein is particularly useful for stabilization of the vertebrae after a spinal decompression surgery. The graft may be coated with a human birth tissue composition. By providing such a coating, adhesion, nerve damage, pain, and graft migration are reduced or eliminated. Further, the incidence of graft rejection is substantially reduced thereby minimizing the potential need for additional surgery. Also provided herein are methods of stabilizing the spine after decompression surgery.

Figure 2:
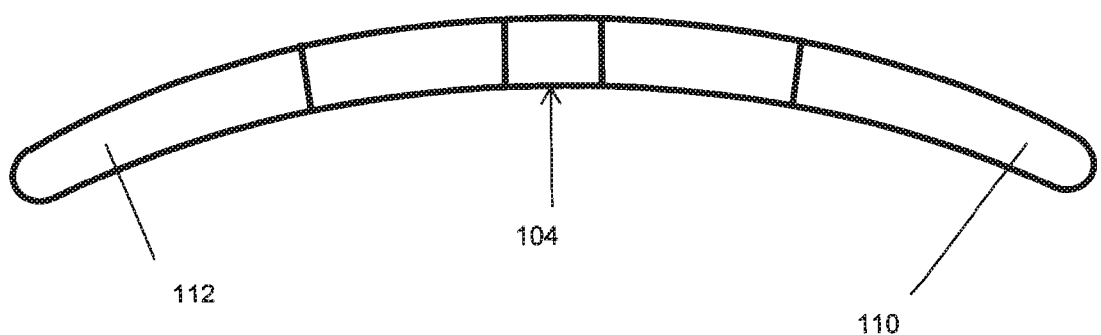
FIG. 2 is a top view of the graft according to the embodiment of FIG. 1.

FIGS. 1 and 2 illustrate a spinal graft 100 according to one embodiment. As illustrated, the graft includes a superior arm 102 having a surface defining a notch 104 positioned at a central region of the superior arm 102 and an inferior arm 106 having a surface defining a notch 108 positioned at a central region of the inferior arm 106. While the arms (102, 106) are generally shown as having blunt or sharp, rectangular edges, the arms (102, 106) may also be generally rounded. The graft 100 further includes a first wing 110 and a second wing 112. While the wings (110, 112) are generally shown as having curved edges, the wings (110, 112) may also have blunt or squared edges. As illustrated in FIG. 2, the graft 100 is formed in a curved manner. By being formed in a curved manner, the graft 100 conforms to the natural shape of the spine. The graft 100 may also have varied cross-sectional shapes to conform to the varied anatomical shapes of the interspinous spaces of the spine. The graft 100 or a portion thereof may also form a barrier to keep the dural sac from connecting to or touching surrounding tissue or bone.

Figure 3:
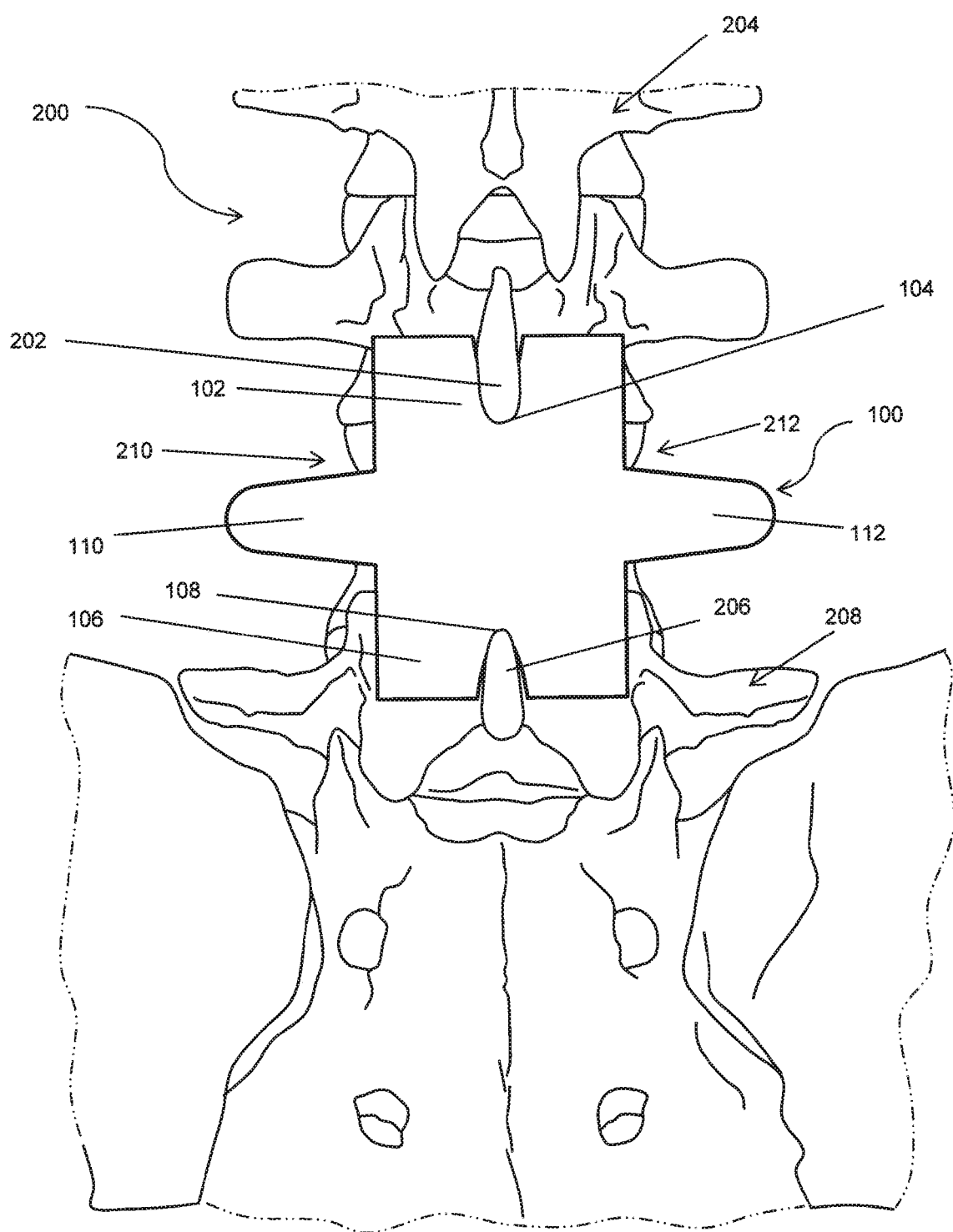
FIG. 3 is a front view of the graft according to the embodiment of FIG. 1 upon positioning in the chosen vertebral region.

FIG. 3 illustrates the spinal graft 100 after placement on or within the spine 200. The notch 104 of the superior arm 102 is positioned to receive and contact against a superior spinous process 202 of a superior vertebra 204. The notch 108 of the inferior arm 106 is positioned to receive and contact against an inferior spinous process 206 of an inferior vertebra 208. The first wing 110 extends into a first vertebral gutter 210. The second wing 112 extends into a second vertebral gutter 212. The location of the spinal graft 100 in the spine 200 is for illustration purposes only as the spinal graft 100 may span multiple vertebra and may be located in various regions of the spine 200.

Figure 4:
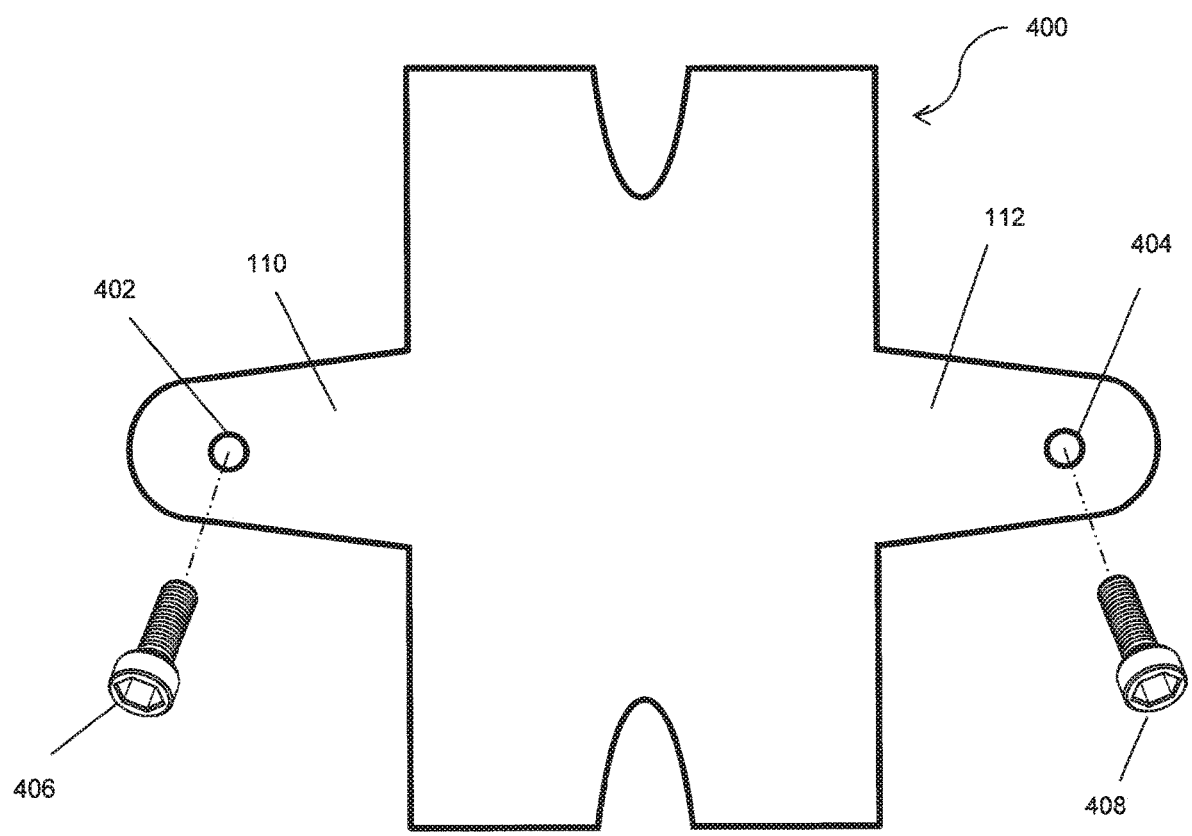
FIG. 4 is a front view of a graft according to an alternative embodiment.

FIG. 4 illustrates a graft 400 according to an alternative embodiment. As illustrated, the graft 400 includes openings (402, 404) centrally located in each wing (110, 112). Each opening (402, 404) is adapted to receive at least one securing device such as, for example, a screw (406, 408).

According to an alternative embodiment (not shown), a rod (or plate) is used to prevent movement and allows the bone graft to heal and fuse. According to such an embodiment, screws are placed above and below the vertebrae fused or stabilized by the graft. After the fusion is completely healed, the screws and rods can be optionally removed.

The grafts as provided here may be made of one or more materials suitable for implantation into the spine of a mammalian patient such as, for example, a human. Materials may be biocompatible with a mammalian patient and/or may have one or more surface coatings or treatments that enhance biocompatible and also reduce or prevent adhesion, nerve damage, pain, and graft migration. Such graft materials may include one or more materials having sufficient bad capability and/or strength to maintain the desired spacing between spinous processes and provide the desired stability. The graft materials may be made of one or more materials that maintain their composition and shape for as long a time as possible without degrading or decomposing or changing shape, such that replacement of the graft is avoided. According to one embodiment, the grafts as provided herein are made from cancellous bone, demineralized cancellous bone, allograft (fresh or fresh-frozen), freeze dried bone allograft, demineralized freeze dried bone allograft, cortical cancellous bone, or a combination thereof. According to a particular embodiment, the graft is made from demineralized cancellous bone as set forth in U.S. Publication No. 2012/0259425, the content of which is incorporated herein by reference in its entirety.

The grafts as provided herein may be coated, treated, or otherwise include an effective amount of a composition including human birth tissue (human birth tissue composition). According to one embodiment, the human birth tissue composition includes one or more placental tissue components. The human birth tissue composition may be formulated as a resorbable adhesion barrier allograft that is applied to the outer surface of the graft. According to an alternative embodiment, the human birth tissue composition may be formulated as an injectable formulation or a flowable formulation that is introduced directly onto or into the grafts as provided herein. According to either embodiment, placental tissue components and amniotic fluid must first be obtained from a seronegative, healthy human. Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Advantageously, the methods that are used to screen for a communicable disease follow the regulations as set forth by the Federal Drug Administration and the American Association of Tissue Banks. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-I I); and syphilis (a non-treponemal or treponemal-specific assay may be performed).

Human birth tissue is preferably recovered from a full-term Cesarean delivery of a newborn. Alternatively, human birth tissue is recovered from a full-term vaginal delivery of a newborn. The subsequent steps of preparing the human birth tissue material are performed in a controlled environment (i.e., certified biological safety cabinet, hood or clean room). Instruments, solutions, and supplies coming into contact with the human birth tissue material during processing are sterile. All surfaces coming in contact with the human birth tissue material intended for transplant are either sterile or draped using aseptic technique.

Once recovered, one or more of the placental tissue components can be removed via a sterile saline solution rinse, blunt dissection, scalpel, or a combination thereof, if necessary. According to one embodiment, the placental globe, umbilical cord, chorionic membrane, and other gelatins, fluids, cells and extracellular matrix are removed and discarded, leaving the amniotic membrane for further processing. Preferably, the human birth tissue material is subject to preparation no more than four hours after recovery to preserve cell viability.

The retained placental tissue components can be placed in a sterile transport solution after aseptic recovery. The sterile transport solution is used to provide an advantageous medium to the natural function of the placental tissue components prior to processing. For example, calcium-rich water can be used as the sterile transport solution to provide a medium to drive undifferentiated cells to become osteogenic when implanted. Throughout the preparation of the human birth tissue material, various methods can be used to drive undifferentiated cells to differentiate into specialized cell types including, but not limited to, transport solutions, soaks, particular temperature ranges, and hyperbaric pressure.

The sterile transport solution may include sodium chloride (NaCl) in a concentration range from typically about 0.1% to typically about 35% by weight. The sterile transport solution can also include one or more of Minimum Essential Medium, Dulbecco's Modified Eagle's Medium, Plasma Lyte-A, human albumin 25% solution, calcium-rich water, alkaline ionized water, or acidic ionized water. After delivery to the processing facility, the weight of the placental tissue components can be determined. Thereafter, the placental tissue components can be transferred aseptically to a sterile dish containing Plasma Lyte-A and stored in a quarantine refrigerator pending further processing. The placental tissue components can be removed from the Plasma Lyte-A and cryopreserved according to methods commonly used in the art. According to one embodiment, the cryopreserved components may then be morselized and formulated into an injectable form and/or a flowable material.

The human birth tissue material compositions as described herein can be optionally mixed with or administered in combination with bioactive agents such as inflammatory inhibitors, antibiotics, cytokines, minerals, growth factors (e.g., fibrin and/or thrombin), wound healing agents, hyaluronic acid, cellular attractant and scaffolding reagents (e.g., fibronectin) antibiotics, chemotherapeutic agents, antigens, antibodies, enzymes, NSAIDs, muscle relaxants, vectors for gene delivery and hormones.

Decompression surgery and subsequent placement of the grafts as provided here are typically performed by an orthopedic surgeon. Surgery is initiated by making a skin incision down the middle of the back over the appropriate vertebrae. The length of the incision depends on the number of laminae that will be subject to the decompression surgery procedure chosen. The strong back muscles are then split and moved to either side of each lamina exposing each vertebra. During a laminectomy, the specific lamina and ligamentum flavum are then removed. Optionally, the surgeon may then retract the dural sac and nerve root to remove any bone spurs or thickened ligaments. The facet joints may then be undercut or trimmed. The spinal fusion to stabilize the spine may then be performed.

According to one embodiment, the spinal fusion or spinal stabilization process may be carried out by placement of a graft as provided herein. Such a process includes the step of positioning a graft between the spinal processes of the superior and inferior vertebra which are above and below the lamina or laminae subject to decompression surgery. The grafts as provided herein may be adapted to be inserted between spinous processes at any region in the spine. Although typically grafts may be inserted in the lumbar region (e.g., between L3 and L5), the grafts as provided herein may be positioned into other regions such as for example, the thoracic or cervical region. The grafts as provided herein may also span multiple vertebra as in the case of removal or alteration of multiple laminae during a laminectomoy or laminotomy. Once positioned, the superior and inferior notches are engaged with the superior and inferior lamina of the superior and inferior vertebra, in no specific order, such that the space between the superior and inferior vertebra is maintained and the spine is stabilized (see e.g., FIG. 3). The first and second wings of the graft are simultaneously positioned within the vertebral gutters. According to a preferred embodiment, the graft remains in place between the laminae without the need for introducing any securing hardware such as screws, plates, or rods.

Alternatively, the graft may be secured by introduction of screws through the first and second wings and into the vertebral gutters (see e.g., FIG. 4). According to such an embodiment, other stabilizing hardware such as, for example, plates or rods may optionally be used in conjunction with the screws.

A kit is also provided that includes one or more grafts as provided herein. The kit may include various sizes of grafts depending on the location of where the graft may be utilized in the spine. The kit may further include tools or other devices useful in selecting, inserting, positioning, and/or securing one or more grafts. Tools and devices may include, for example, one or more pins, screws, rods, plates, wires, cables, straps, surgical rope, sutures, or other devices typically used for positioning and securing the grafts. The kit further includes at least one set of instructions.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

We claim:

1. A method of stabilizing a vertebral region of a spine following a decompression surgery comprising
    performing a decompression surgery;
    providing a graft comprising;
        a rounded superior arm having a surface defining a notch positioned at a central region of the superior arm to receive and contact against an inferior edge of a spinous process of a superior vertebra;
        a rounded inferior arm having a surface defining a notch positioned at a central region of the inferior arm to receive and contact against a superior edge of a spinous process of an inferior vertebra;
        a first wing for extending into a first vertebral gutter; and
        a second wing for extending into a second vertebral gutter, the first and second wing having curved edges;
        wherein an effective amount of a human birth tissue material composition is deposited on an outer surface of the graft,
    engaging the notch of the superior arm with an inferior edge of a spinous process of a superior vertebra in a lumbar region of the spine; and
    engaging the notch of the inferior arm with an superior edge of a spinous process of an inferior vertebra in a lumbar region of the spine,
    wherein the vertebral region of the spine is stabilized.

2. The method of claim 1, further comprising the step of securing the graft to the vertebral region with at least one screw.

3. The method of claim 1, further comprising at least one area defining an opening for receiving at least one screw for securing the graft.

4. The method of claim 3, wherein at least one opening is located in each of the first and second wings such that a screw is configured to be secured within the first and second vertebral gutters.

5. The method of claim 1, wherein the graft is prepared from cancellous bone, demineralized cancellous bone, allograft (fresh or fresh-frozen), freeze dried bone allograft, demineralized freeze dried bone allograft, cortical cancellous bone, or a combination thereof.

6. The method of claim 1, wherein the birth tissue material composition comprises one or more components of the placental organ.

7. The method of claim 6, wherein the one or more of the placental tissue components is selected from the group consisting of the placental globe, the umbilical cord, the umbilical cord blood, the chorionic membrane, the amniotic membrane, the Wharton's jelly, the amniotic fluid, and other placental gelatins, cells, and extracellular material.

8. A kit for stabilizing the spine following a decompression surgery comprising
    one or more grafts comprising;
        a rounded superior arm having a surface defining a notch positioned at a central region of the superior arm to receive and contact against an inferior edge of a spinous process of a superior vertebra;
        a rounded inferior arm having a surface defining a notch positioned at a central region of the inferior arm to receive and contact against a superior edge of a spinous process of an inferior vertebra;
        a first wing for extending into a first vertebral gutter; and
        a second wing for extending into a second vertebral gutter, the first and second wing having curved edges;
    a composition including human birth tissue deposited on an outer surface of the graft;
    optionally, at least one screw for securing the graft to the spine; and
    instructions for use thereof.

9. The kit of claim 8, wherein the one or more grafts are sized based on the location of utilization in the spine.

* * * * *